(12) United States Patent
Hart

(10) Patent No.: US 8,652,147 B2
(45) Date of Patent: Feb. 18, 2014

(54) DEVICE FOR ISOLATING AND REMOVING TISSUE FROM A BODY CAVITY

(75) Inventor: Charles C. Hart, Summerville, SC (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 891 days.

(21) Appl. No.: 11/549,701

(22) Filed: Oct. 16, 2006

(65) Prior Publication Data
US 2007/0135781 A1 Jun. 14, 2007

Related U.S. Application Data

(60) Provisional application No. 60/726,637, filed on Oct. 14, 2005.

(51) Int. Cl.
A61B 17/24 (2006.01)
(52) U.S. Cl.
USPC .......................................................... 606/114
(58) Field of Classification Search
USPC ................... 606/114, 113, 127, 128; 604/327
See application file for complete search history.

(56) References Cited

U.S. PATENT DOCUMENTS

| 30,471 | A | 10/1860 | Dudley |
| 1,609,014 | A | 11/1926 | Dowd |
| 3,476,114 | A | 11/1969 | Shannon, et al. |
| 3,476,115 | A | 11/1969 | Graeff et al. |
| 4,428,375 | A * | 1/1984 | Ellman .......................... 606/151 |
| 4,732,150 | A | 3/1988 | Keener, Jr. |
| 4,741,335 | A | 5/1988 | Okada |
| 4,991,593 | A | 2/1991 | Levahn |
| 5,037,379 | A | 8/1991 | Clayman et al. |
| 5,074,867 | A | 12/1991 | Wilk |
| 5,143,082 | A | 9/1992 | Kindberg et al. |
| 5,147,371 | A | 9/1992 | Washington et al. |
| 5,176,687 | A | 1/1993 | Hasson et al. |
| 5,190,542 | A | 3/1993 | Nakao et al. |
| 5,190,555 | A | 3/1993 | Wetter et al. |
| 5,190,561 | A | 3/1993 | Graber |
| 5,192,284 | A | 3/1993 | Pleatman |
| 5,192,286 | A | 3/1993 | Phan et al. |

(Continued)

FOREIGN PATENT DOCUMENTS

| DE | 25796 | 1/1884 |
| DE | 4216165 | 11/1992 |

(Continued)

OTHER PUBLICATIONS

European Patent Office, International Search Report and The Written Opinion of the International Searching Authority for PCT application No. PCT/US2006/060007 mailed Mar. 2, 2007.

(Continued)

Primary Examiner — S. Thomas Hughes
Assistant Examiner — Sarah Simpson
(74) Attorney, Agent, or Firm — John F. Heal; Patrick Y. Ikehara

(57) ABSTRACT

A tissue isolation and removal device has a containment pouch that is opened and supported by the device. The pouch has two open/close portions both able to be closed and reopened. One portion positioned away from tissue being inserted in the pouch and covering the other portion to enclose or isolate any tissue captured in the other portion.

19 Claims, 18 Drawing Sheets

(56) References Cited

U.S. PATENT DOCUMENTS

| | | |
|---|---|---|
| 5,195,507 A | 3/1993 | Bilweis |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,279,548 A | 1/1994 | Essig et al. |
| 5,308,327 A | 5/1994 | Heaven et al. |
| 5,312,416 A | 5/1994 | Spaeth et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,366,460 A | 11/1994 | Eberbach |
| 5,368,597 A | 11/1994 | Pagedas |
| 5,417,684 A | 5/1995 | Jackson et al. |
| 5,417,697 A | 5/1995 | Wilk et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| RE35,164 E | 3/1996 | Kindberg et al. |
| 5,509,923 A | 4/1996 | Middleman et al. |
| 5,524,633 A | 6/1996 | Heaven et al. |
| 5,535,759 A | 7/1996 | Wilk |
| 5,601,572 A | 2/1997 | Middleman et al. |
| 5,611,803 A | 3/1997 | Heaven et al. |
| 5,613,973 A | 3/1997 | Jackson et al. |
| 5,632,746 A | 5/1997 | Middleman et al. |
| 5,643,283 A | 7/1997 | Younker |
| 5,647,372 A * | 7/1997 | Tovey et al. ............... 600/562 |
| 5,655,657 A | 8/1997 | Roshdy |
| 5,656,012 A | 8/1997 | Sienkiewicz |
| 5,679,423 A | 10/1997 | Shah |
| 5,681,324 A * | 10/1997 | Kammerer et al. .......... 606/113 |
| 5,720,754 A | 2/1998 | Middleman et al. |
| 5,735,289 A | 4/1998 | Pfeffer et al. |
| 5,741,271 A | 4/1998 | Nakao et al. |
| 5,749,879 A | 5/1998 | Middleman et al. |
| 5,759,187 A | 6/1998 | Nakao et al. |
| 5,779,716 A | 7/1998 | Cano et al. |
| 5,782,839 A | 7/1998 | Hart et al. |
| 5,785,677 A | 7/1998 | Auweiler |
| 5,809,621 A * | 9/1998 | McCree et al. ............... 24/399 |
| 5,820,628 A | 10/1998 | Middleman et al. |
| 5,853,374 A | 12/1998 | Hart et al. |
| 5,904,690 A | 5/1999 | Middleman et al. |
| 5,947,978 A | 9/1999 | Holsinger |
| 5,971,995 A * | 10/1999 | Rousseau ..................... 606/114 |
| 5,980,544 A | 11/1999 | Vaitekunas |
| 5,997,547 A | 12/1999 | Nakao et al. |
| 6,004,330 A | 12/1999 | Middleman et al. |
| 6,015,415 A | 1/2000 | Avellanet |
| 6,019,770 A | 2/2000 | Christoudias |
| 6,059,793 A | 5/2000 | Pagedas |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,350,267 B1 | 2/2002 | Stefanchik |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,575,988 B2 | 6/2003 | Rousseau |
| 6,805,699 B2 | 10/2004 | Shimm |
| 6,814,739 B2 | 11/2004 | Secrest et al. |
| 6,958,069 B2 | 10/2005 | Shipp et al. |
| 6,986,774 B2 | 1/2006 | Middleman et al. |
| 7,041,055 B2 | 5/2006 | Young et al. |
| 7,115,125 B2 | 10/2006 | Nakao et al. |
| 7,270,663 B2 | 9/2007 | Nakao et al. |
| 7,416,338 B2 * | 8/2008 | Ausnit ......................... 383/64 |
| 7,547,310 B2 | 6/2009 | Whitfield |
| 7,618,437 B2 | 11/2009 | Nakao |
| 7,670,346 B2 | 3/2010 | Whitfield |
| 2003/0100919 A1 | 5/2003 | Hopkins et al. |
| 2004/0087969 A1 | 5/2004 | Kayan |
| 2004/0097960 A1 | 5/2004 | Terachi et al. |
| 2004/0138587 A1 | 7/2004 | Lyons |
| 2004/0254573 A1 | 12/2004 | Dycus et al. |
| 2005/0165411 A1 | 7/2005 | Orban |
| 2005/0267489 A1 | 12/2005 | Secrest et al. |
| 2005/0267492 A1 | 12/2005 | Poncet et al. |
| 2006/0052799 A1 | 3/2006 | Middleman et al. |
| 2006/0173468 A1 | 8/2006 | Simmon et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0276805 A1 | 12/2006 | Yu |
| 2007/0088370 A1 | 4/2007 | Kahle et al. |
| 2008/0033451 A1 | 2/2008 | Rieber et al. |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2009/0043315 A1 | 2/2009 | Moon |
| 2009/0082779 A1 | 3/2009 | Nakao |
| 2009/0192510 A1 | 7/2009 | Bahney |
| 2010/0076451 A1 | 3/2010 | Zwolinski et al. |
| 2010/0152609 A1 | 6/2010 | Zwolinski et al. |

FOREIGN PATENT DOCUMENTS

| | | |
|---|---|---|
| DE | 197 07 361 | 8/1998 |
| EP | 499243 A1 | 8/1992 |
| EP | 0 947 166 | 10/1999 |
| JP | 5-115493 | 5/1993 |
| JP | 6-154161 | 6/1994 |
| SU | 1537229 | 4/1987 |
| WO | WO 93/15671 | 8/1993 |
| WO | WO 93/24063 | 12/1993 |
| WO | WO 94/13215 | 6/1994 |
| WO | WO 2003/105674 | 12/2003 |
| WO | WO 2007/081601 | 7/2007 |

OTHER PUBLICATIONS

The International Bureau of WIPO, International Preliminary Report on Patentability for PCT Application No. PCT/US2006/060007 mailed Apr. 24, 2008.

United States Surgical, Tyco Healthcare Group LP, Autosuture Endo Catch Single-Use Specimen Pouch Frequently Asked Questions and Features and Benefits (Web pages) 2004 4 pages.

United States Surgical, Tyco Healthcare Group LP, Autosuture Endocatch Gold 10 mm Single-Use Specimen Pouch, 10000-25912, Product Information Data Sheet Feb. 2004, 2 pages.

United States Surgical, Tyco Healthcare Group LP, Autosuture Endocatch II Single-Use Specimen Pouch, 10000-19724, Product Information Data Sheet, Aug. 2002, 2 pages.

Conmed Corporation, EndoSurgery Products, Hand Held Laparoscopic Instruments, Product Descriptions (Web pages), 2004, 3 pages.

Cook Group Inc., CookUrological, Cook® Drainage Pouch Sets, Product Description (Web page), 2003, 1 page.

Johnson & Johnson Gateway LLC, Ethicon Endo-Surgery Inc., Endoscopic Product Family, Endopouch Retriever Specimen Retrieval Bag Product Description (Web Page), 2000-2005 1 page.

European Patent Office, ISR/WO for Patent Application No. PCT/US2006/060007 mailed Mar. 2, 2007.

The International Bureau of WIPO, The International Preliminary Report on Patentability for International Application No. PCT/US2006/06007, mailed Apr. 24, 2008.

European Patent Office, International Search Report and Written Opinion of the International Searching Authority for International Application No. PCT/US2006/06022 mailed Jun. 5, 2007.

The International Search Authority, International Search Report and Written Opinion for International Application No. PCT/US2010/052190, mailed Feb. 3, 2011.

(56) References Cited

OTHER PUBLICATIONS

The International Bureau of WIPO, International Preliminary Report on Patentability, for International Application No. PCT/US2010/052190, entitled Single Incision Laparoscopic Tissue Retrieval System, mailed Apr. 11, 2012.

International Searching Authority, The International Search Report and Written Opinion for International Application No. PCT/US2011/054647, entitled Laparoscopic Tissue Retrieval System, dated Feb. 21, 2012.

* cited by examiner

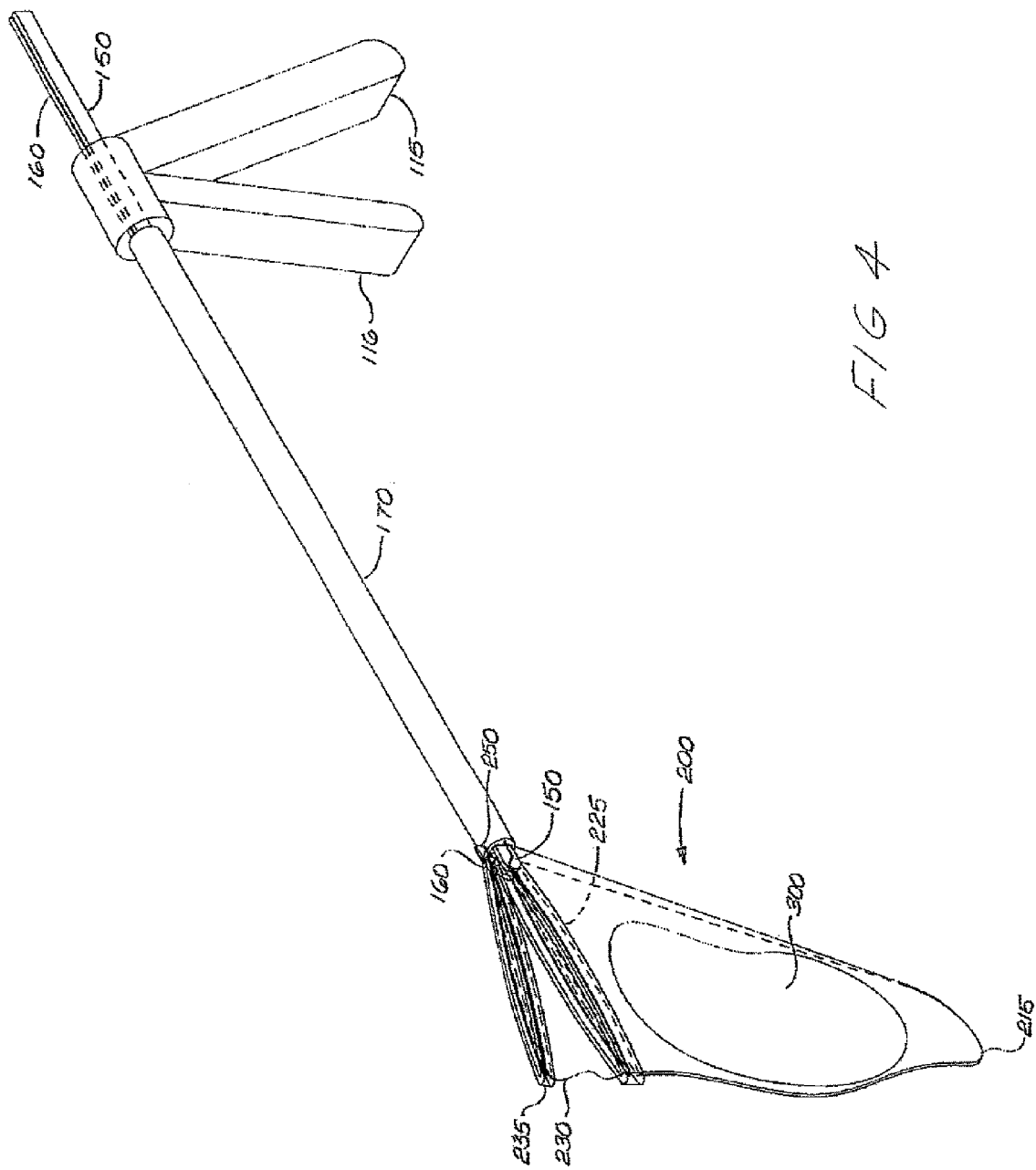

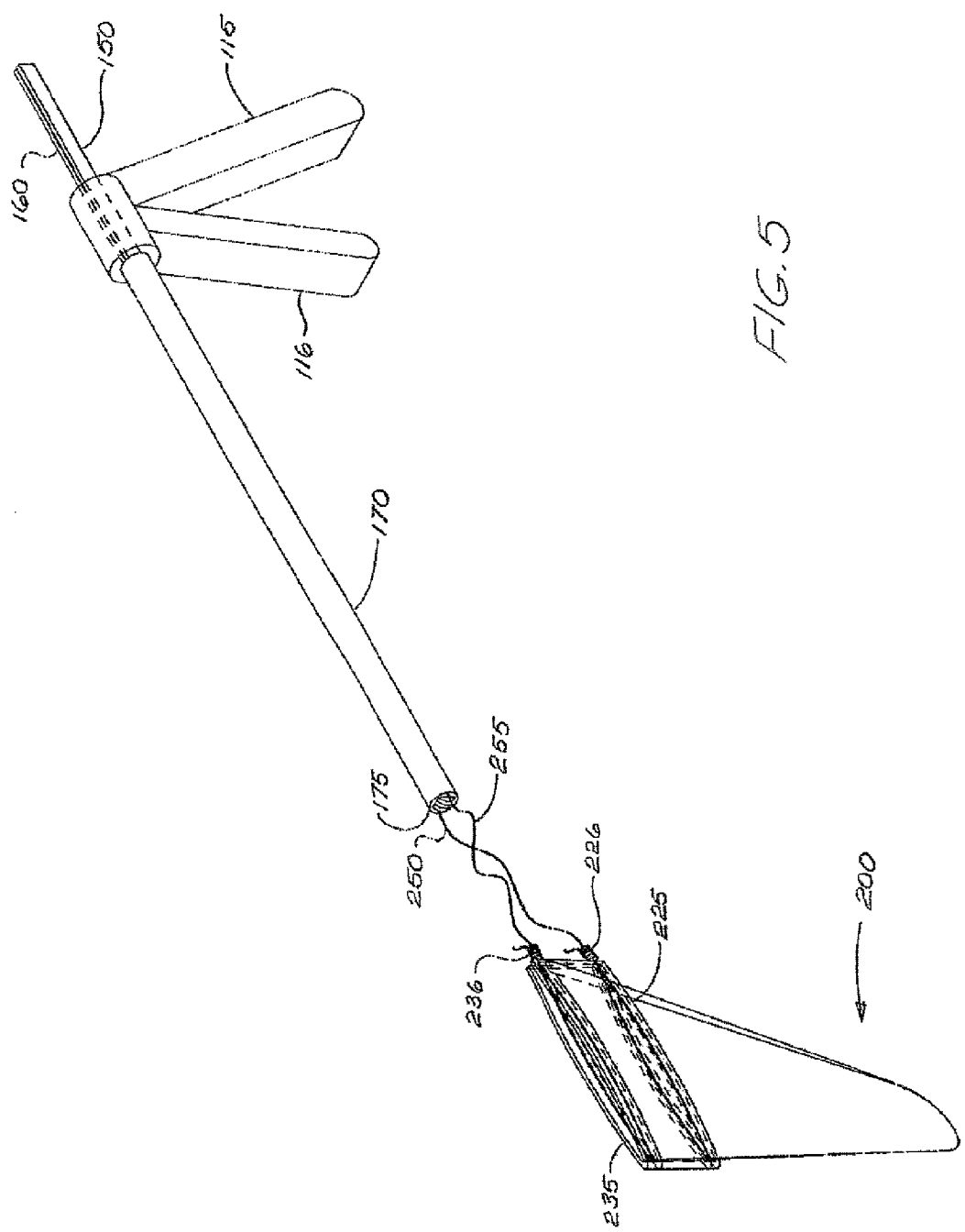

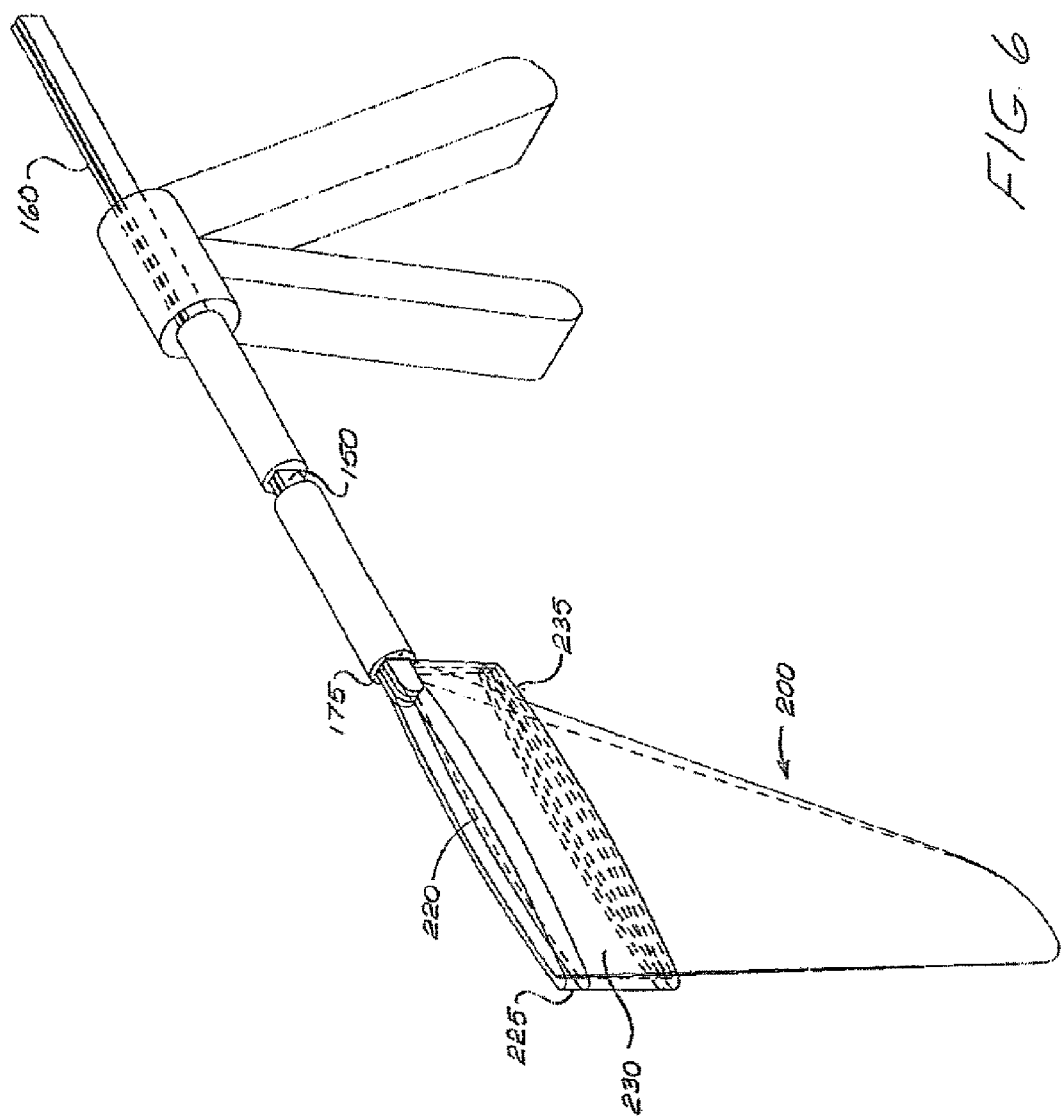

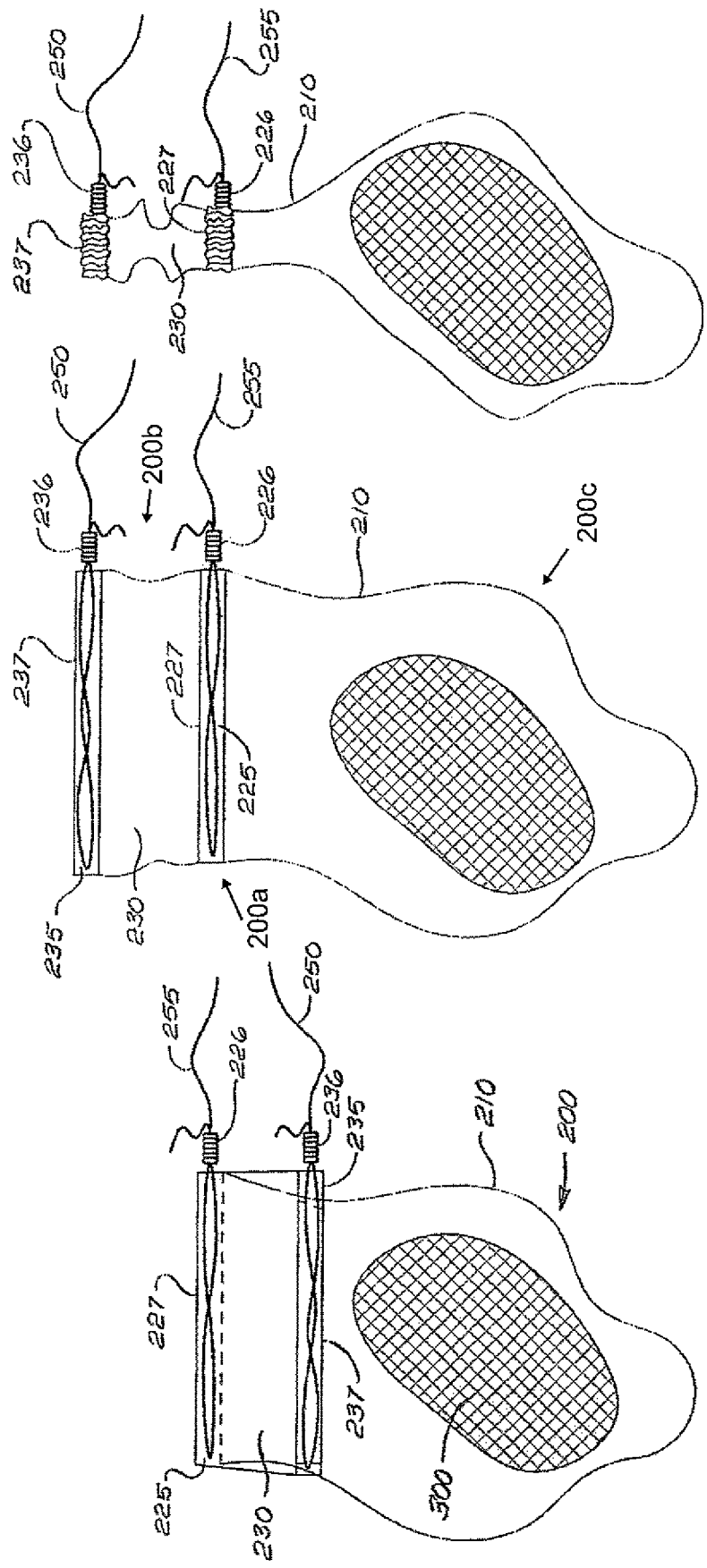

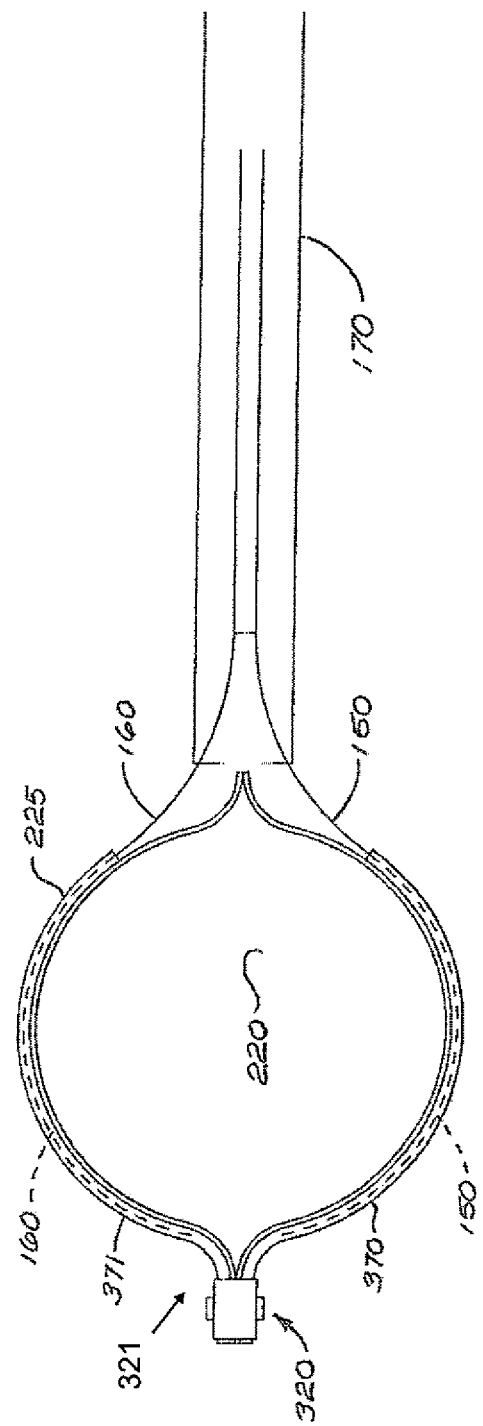

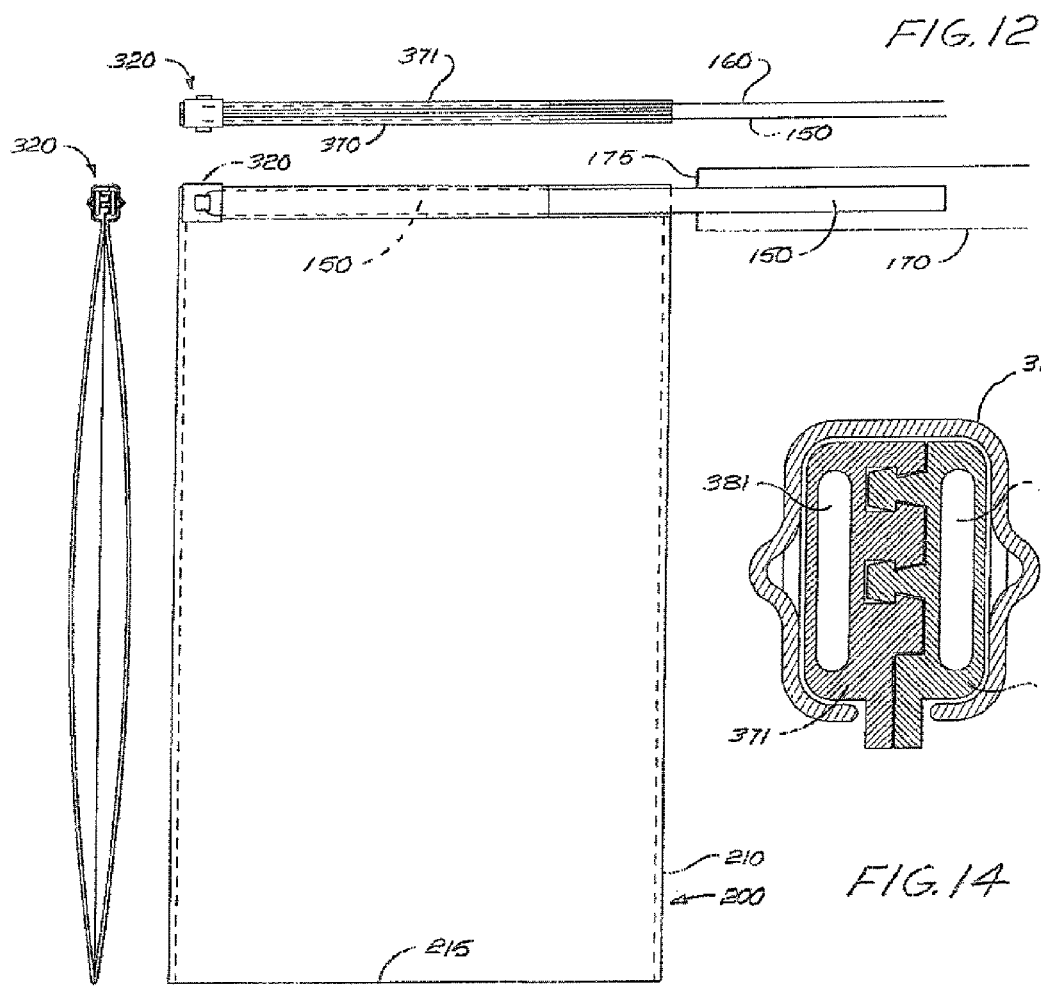

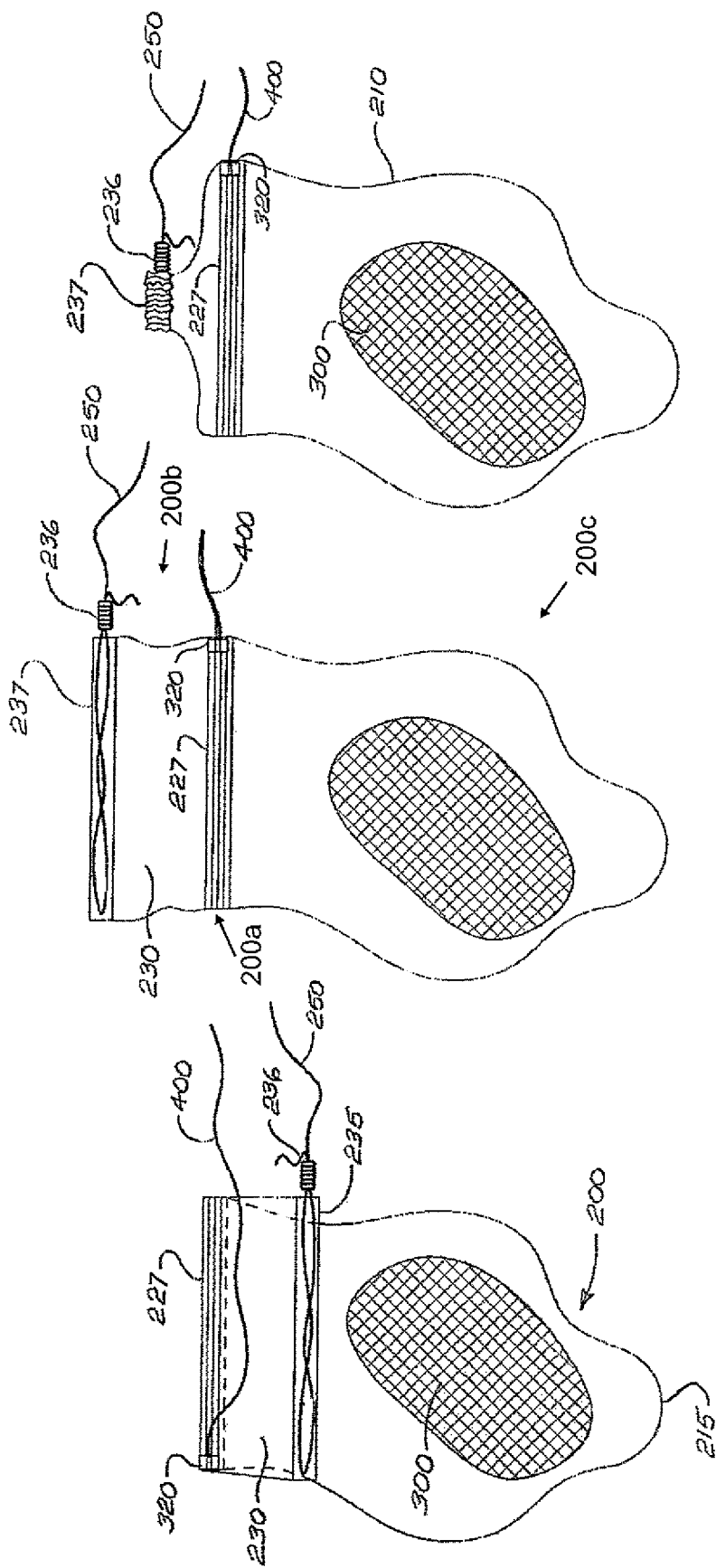

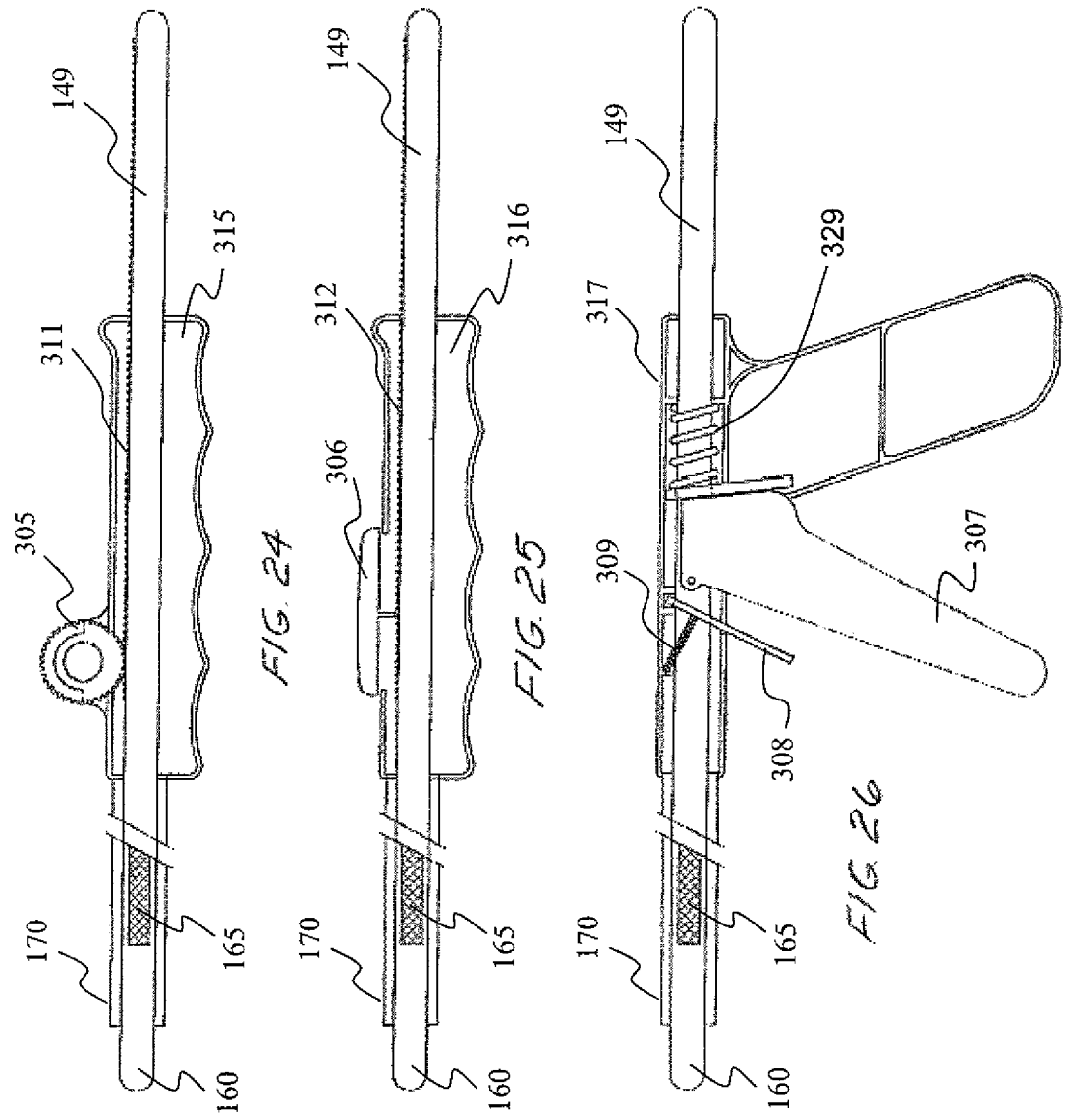

DEVICE FOR ISOLATING AND REMOVING TISSUE FROM A BODY CAVITY

CROSS-REFERENCE TO RELATED APPLICATIONS

This application claims the benefit of U.S. Provisional Application No. 60/726,637, filed Oct. 14, 2005, the disclosure of which is hereby incorporated by reference as if set forth in full herein.

BACKGROUND

This invention relates generally to apparatus and methods for capturing and retrieving tissue from body cavities and in particular to a specimen retrieval bag device.

Laparoscopic surgery is typically performed through trocars, which provide access across the abdominal wall and into the abdominal cavity. In some of surgeries, tissue disposed within the abdominal cavity is cut and removed from the body. However, removal of such tissue from the body may prove difficult due to the limited confines inherent with laparoscopic surgery and the available laparoscopic surgical instruments. Also, such tissue may include an infected or cancerous mass or organ, as well as blood, bile and other liquids, all referred to herein as tissue, which may pose infection issues or other complications if left within the body.

It is desirable to grasp, capture, retain and enclose this tissue while in the body cavity, and then remove the enclosed tissue through the trocar or incision. Containment of the tissue as quickly as possible with minimal disturbance to the surgical site is also desirable. A generally compact and single unit device would also prove desirable as devices generally bulky and complicated have several shortcomings and lack optimal efficiency in particular with the limited space in operating rooms and access ports in the body cavity. In general, such bulky or complicated device also lack optimal efficiency during insertion and removal of material and are deficient in maintaining directional orientation of the enclosed tissue during extracorporeal usage.

SUMMARY

Generally, the present invention provides a tissue isolation and removal device. In one aspect, the tissue isolation and removal device comprises an elongate shaft having at least one support arm extending from one end of the elongate shaft, a containment bag having a first, second and third portion, the first portion of the containment bag supported by the at least one support arm, a first drawstring coupled to the first portion and a second drawstring coupled to the second portion.

In one aspect, a tissue isolation and removal device comprises a containment bag has a first, second and third portion. The first portion of the containment bag supported by the at least one support arm, a first drawstring is coupled to the first portion and a second drawstring is coupled to the second portion of the bag.

In one aspect, a tissue isolation and removal device comprises an elongate shaft, an actuator and a containment bag. The elongate shaft has a proximal end, a distal end, and a central core support. The central core support is substantially rectangular and movable out of the proximal end and the distal end of the shaft and has at least one support arm extending from the central core support. An actuator is connected to another end of the elongate shaft. The actuator has a trigger connected to a ratchet-clutch to regulate movement of the central core support. A containment bag has a first, second and third portion. The first portion of the containment bag is supported by the at least one support arm. The third portion of the bag is larger than the second portion of the bag and the second portion of the bag is foldable over the first portion. A first drawstring is coupled to the first portion of the bag and a clasp is connected to the first portion of the bag and the first drawstring. In one aspect, a reinforcement insert provides a reinforcing means for the at least one support arm that is releasable from the at least one support arm.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIG. 4 is a perspective view of a collection bag or pouch in accordance with various aspects of the present invention in a closed condition;

FIG. 5 is a perspective view of a collection bag or pouch in accordance with various aspects of the present invention prepared for retrieval through an access port;

FIG. 6 is a perspective view of a collection bag or pouch and deployment device in accordance with various aspects of the present invention;

FIG. 7 is a side view of a collection bag or pouch in accordance with various aspects of the present invention in for example a first, open condition;

FIG. 8 is a side view of a collection bag or pouch in accordance with various aspects of the present invention in for example a second, open condition;

FIG. 9 is a side view of a collection bag or pouch in accordance with various aspects of the present invention in for example a third, closed, sealed condition;

FIG. 10 is a top view of a collection bag or pouch and a sealing member in accordance with various aspects of the present invention;

FIG. 11 is a side view of a sealing member in accordance with various aspects of the present invention;

FIG. 12 is a top view of a sealing member in accordance with various aspects of the present invention;

FIG. 13 is a front end, distal view of a sealing member in accordance with various aspects of the present invention;

FIG. 14 is an enlarged section view of a collection bag or pouch and sealing member in accordance with various aspects of the present invention;

FIG. 15 is an enlarged top view of a collection bag or pouch and sealing member in accordance with various aspects of the present invention;

FIG. 17 is a side view of a collection bag or pouch and sealing member in accordance with various aspects of the present invention in, for example, a first condition;

FIG. 18 is a side view of a sealing member in accordance with various aspects of the present invention in, for example, a second condition;

FIG. 19 is a side view of a sealing member in accordance with various aspects of the present invention in, for example, a third condition;

FIG. 24 is a side section view of a handle and actuator mechanism in accordance with various aspects of the present invention;

FIG. 25 is a side section view of a handle and actuator mechanism in accordance with various aspects of the present invention;

FIG. 26 is a side section view of a handle and actuator mechanism in accordance with various aspects of the present invention;

DETAILED DESCRIPTION

Generally, the present invention provides a tissue isolation and removal device that isolates subject tissue and has a secondary closure member that covers the primary opening of the pouch or bag of the device so that removal of the device from the body cavity does not result in contamination of the incision or retrieval site. A user may insert the device through an access port of appropriate size and subsequently deploy and/or open the pouch or bag, place tissue into the bag, and subsequently close the pouch or bag in a series of sequential operations of a single handle-mounted lever. The pouch or bag is closed and a secondary cover shield or foldable/inverted portion is put in place, the device or portions thereof may be removed from the device and/or the access port. The closed pouch or bag may be withdrawn from the access site.

Figure 1:
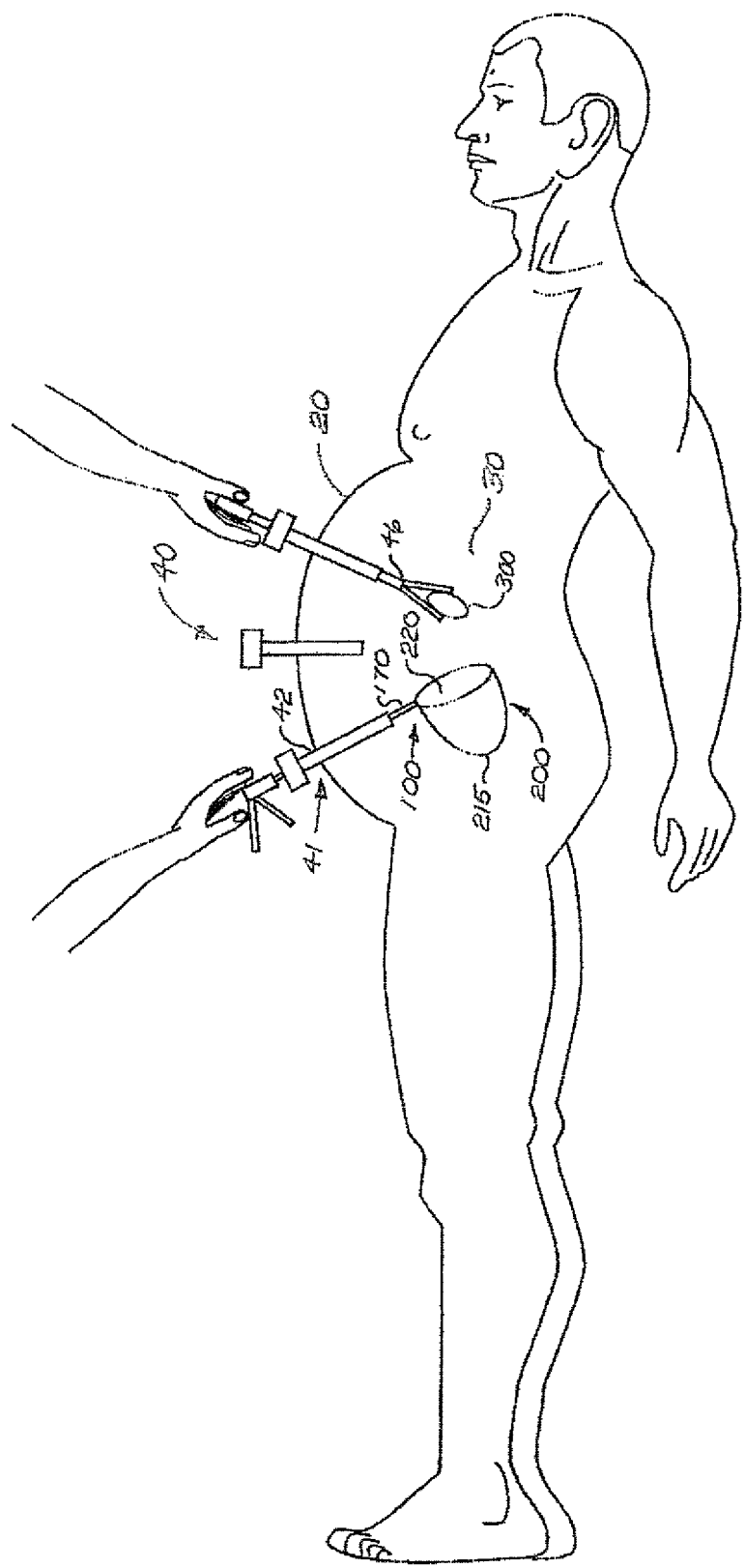
FIG. 1 is an illustration of a laparoscopic surgical setting that uses a collection bag or pouch in accordance with various aspects of the present invention.
Figure 2:
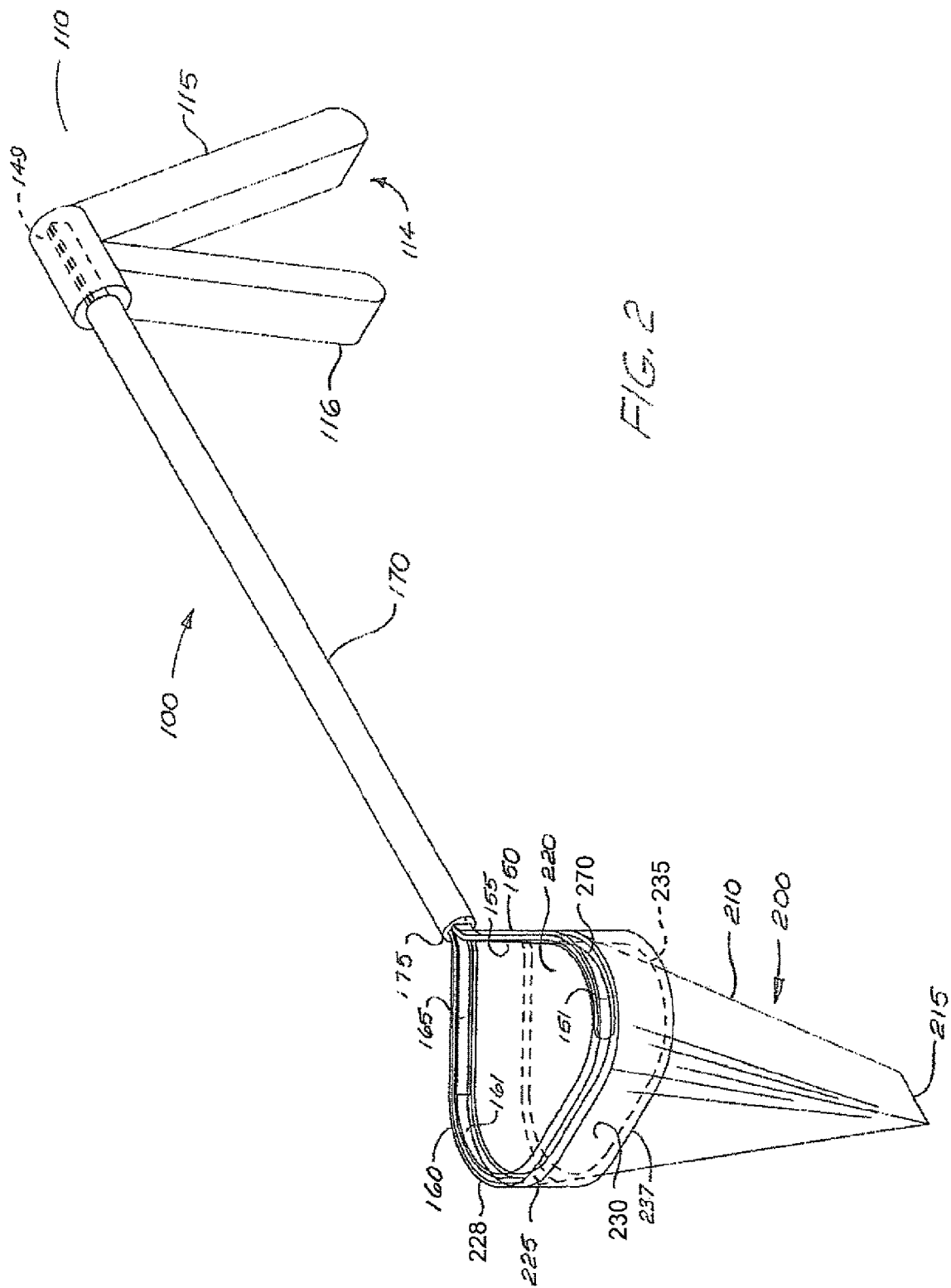
FIG. 2 is a perspective view of a collection bag or pouch in accordance with various aspects of the present invention.

In FIG. 1 a minimally invasive or laparoscopic surgical procedure set-up is shown. Access ports 40, e.g., trocars, are inserted through a body wall 20 into a body cavity 30, such as an abdomen. A positive gas pressure is introduced and maintained through the access ports 40. A variety of elongated surgical instruments, such as graspers, scissors, knives, sponges, retractors and the like, may be used to accomplish the surgical procedure. Such instruments are designed to allow a surgeon to perform surgery in a closed environment rather than an open environment. The instruments can be designed to mimic those used in an open surgery but at a much smaller scale and at a much greater distance than that of open surgery.

As illustrated, a laparoscopic surgical grasper 46 is holding a portion of tissue 300 or an organ to be deposited within a laparoscopic retrieval pouch or bag 200. The pouch 200 has an open portion 220 and a closed portion 215 and an elongate shaft 170 that holds and supports the pouch or bag 200. The specimen 300 is isolated from adjacent tissue by the material of the bag or pouch 200, which in one aspect is gas and watertight. The bag or pouch 200 is closed when the specimen 300 is fully within the bag 200. In one procedure, the access port or trocar 41 is removed so that the pouch or bag 200 may be withdrawn through the incision defect 42 in a closed and sealed condition. If the specimen 300 is too large or bulky, the top, open, portion 220 of the pouch or bag 200 may be drawn through the incision defect 42 and subsequently re-opened so that the contents 300 may be withdrawn from the pouch or bag 200 without contacting the incision defect 42 itself. In some cases, a chopper or morcellator may be introduced into the pouch or bag 200 to reduce the bulk of the contents 300 prior to withdrawal through the incision defect 42.

In FIGS. 2 through 6, a laparoscopic device 100 for isolating and removing tissue or organs 300 from a body cavity 30 comprises an elongate tubular body or shaft 170 having a proximal end 110 and a distal end 175. In one aspect, the shaft 170 has a length sufficient for use through a laparoscopic access port, a movable central core support 149 comprises elongate support arms 150, 160 and a removable pouch or bag 200 associated with the support arms 150, 160 of the central core support 149. The proximal end 110 of the shaft 170 is associated with an actuator 114 having a first stationary handle 115 and a second, opposed, movable handle 116. The two opposed handles 115, 116 cooperate to provide a force to axially move the core support 149. The core support 149 may be selectively moved between a first condition or position where the distal end portions of the support arms 150, 160 are contained within the shaft 170 and a second position where the distal end portions of the support arms 150, 160 are extended from the distal end 175 of the shaft 170.

As such, motion associated with the opposed handle members 115, 116 urges the central core member 149 to an extended position beyond the distal end 175 of the elongate body 170. The central core support 149 generally comprises a pair of elongate support arms 150, 160 sized and configured to slide within the elongate shaft 170 axially without rotating. The lumen of the elongate shaft 170 is sized and configured to allow axial movement of the central core support 149 and prevent rotation of the central core support 149. The distal end portion 151 of the first support arm 150 of the central core support 149 is configured to assume a shape as it is urged distally from the elongate shaft 170. The distal end portion 161 of the second support arm 160 of the central core support 149 is configured to assume a shape as it is urged distally from the elongate shaft 170. The two support arms 150, 160 of the central core support 149 are configured to separate at a distance so as to supply an opening force to an associated pouch or bag 200. In one aspect, the support arms 150, 160 are formed from a rigid plastic having a generally rectangular cross-section. Each support arm 150, 160 in one aspect comprises a proximal end portion sized and configured to engage a portion of the actuator 114 thereby translating motion from the actuator to the support arms 150, 160.

The distal end portions 151, 161 of each of respective support arms 150, 160 of the central core support 149 are sized configured to fit within side-pockets or channels 270, 228 of the pouch or bag 200. Additionally, the distal end portions 151, 161 are configured to maintain a preformed shape and distance apart from each other. The strength of the support arms 150, 160 to maintain the preformed shape and distance in one aspect is supplied, in part and one aspect, by reinforcement inserts 155, 165 that are pre-shaped to a particular or predetermined condition. The inserts 155, 165 may be of a spring metal, stainless steel or Nickel-Titanium having "shape memory" characteristics. The inserts 155, 165 are placed at a location along the length of the support arms 150, 160 where they will provide the particular or predetermined shape and separation between the two support arms 150, 160 and, additionally, allow, for example, a distal-most section of the distal end portions 151, 161 of the support arms 150, 160 to bend or conform to the tension of the associated containment pouch or bag 200. In this way, in one aspect, a generally curved shape is maintained at the opening or open end 220 of the pouch or bag 200. A reinforcement insert is releasably connected to the at least one support arm. As such, in one aspect, one or more reinforcement inserts 155, 165 are incorporated in a first hollow channel 225 and are arranged to receive at least one of the support arms 150, 160. The reinforcement insert in one aspect is a sleeve having a proximal open end and a distal open end. As such, the at least one support arm can extend through and thus out of both ends. Additionally, a plurality of reinforcement inserts or sleeves may be provided to assist in supporting different and multiple areas of the bag and/or to provide different opening configurations or opening sections of the bag.

In one aspect, the containment pouch 200 comprises a plastic bag having a closed end 215, an open end 220 and an inverted portion 230. The containment pouch 200 is provided with a first hollow channel 225 formed circumferentially about the open end 220 and a second hollow channel 235 formed circumferentially about the lip or open end 237 of the inverted portion 230. The first hollow channel 225 in one aspect forms a continuous pocket for the support members 150, 160 of the deployment device 100 and a drawstring 255 for closing the containment pouch 200. The second hollow channel 235 in one aspect forms a continuous channel for the drawstring 250 associated with inverted portion 230. The drawstrings 250, 255 in one aspect each have a slipknot 236, 226 in position adjacent to the proximally facing openings of the hollow channels 235, 225 for drawing the openings 220, 237 of the pouch 200 closed.

Figure 3:
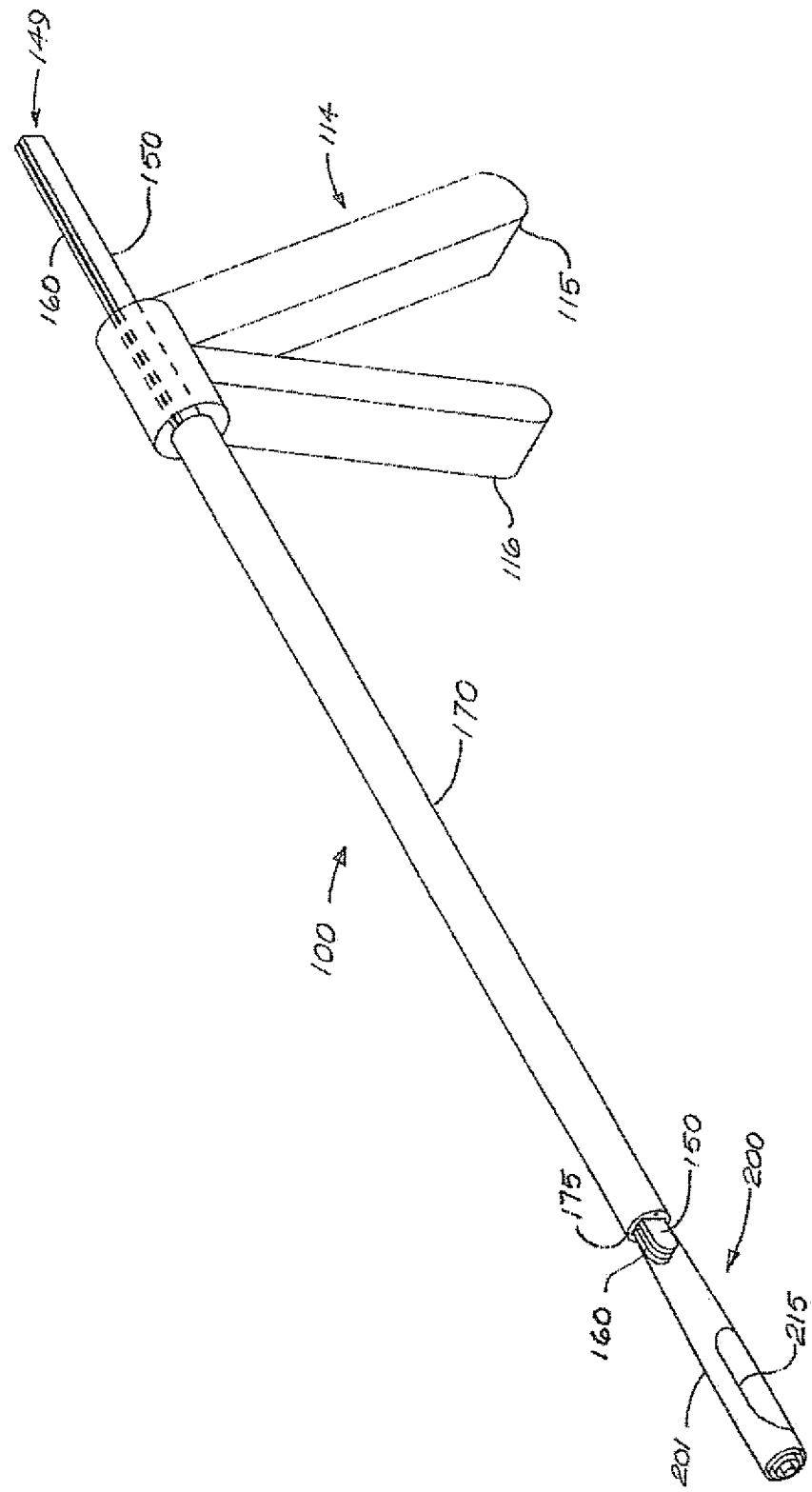
FIG. 3 is a perspective view of a collection bag or pouch in accordance with various aspects of the present invention prepared for introduction through an access port.
Figure 16:
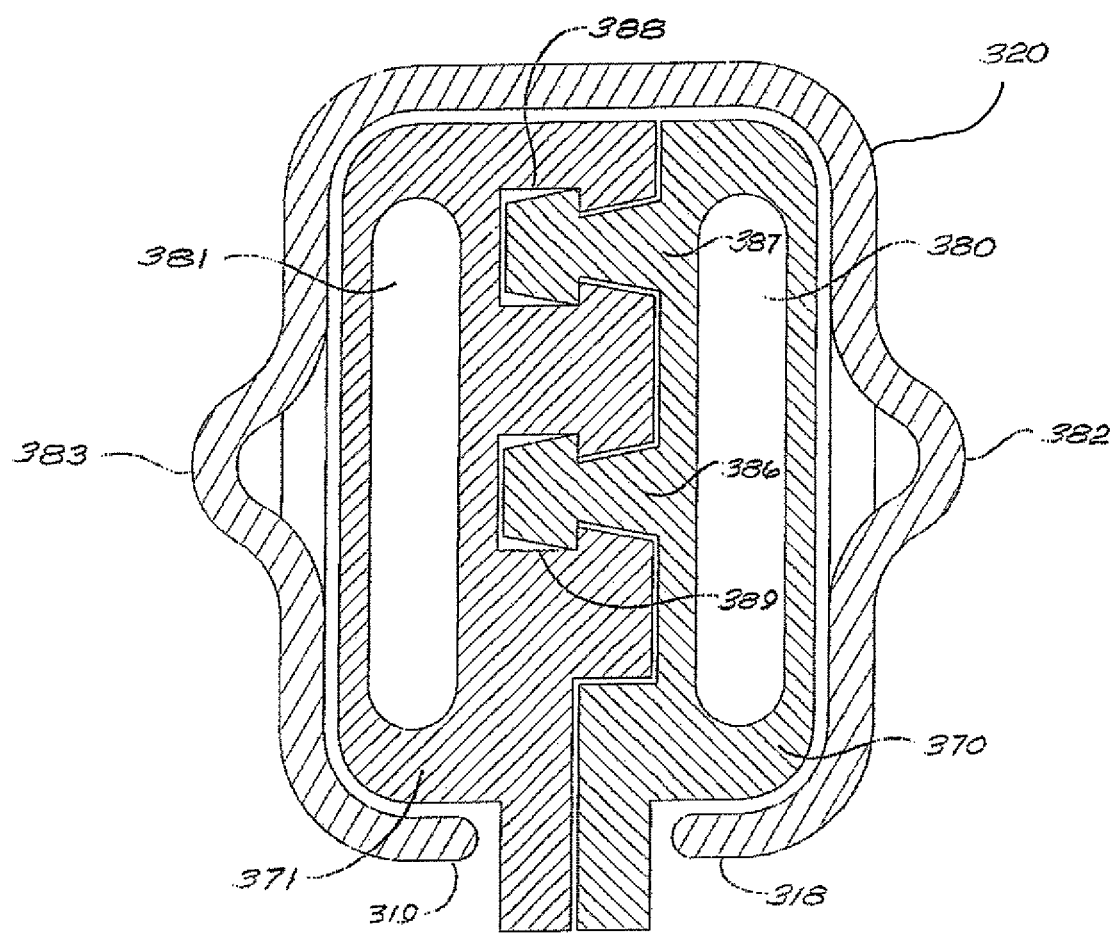
FIG. 16 is an enlarged section view of a collection bag or pouch and sealing member in accordance with various aspects of the present invention.
Figure 20:
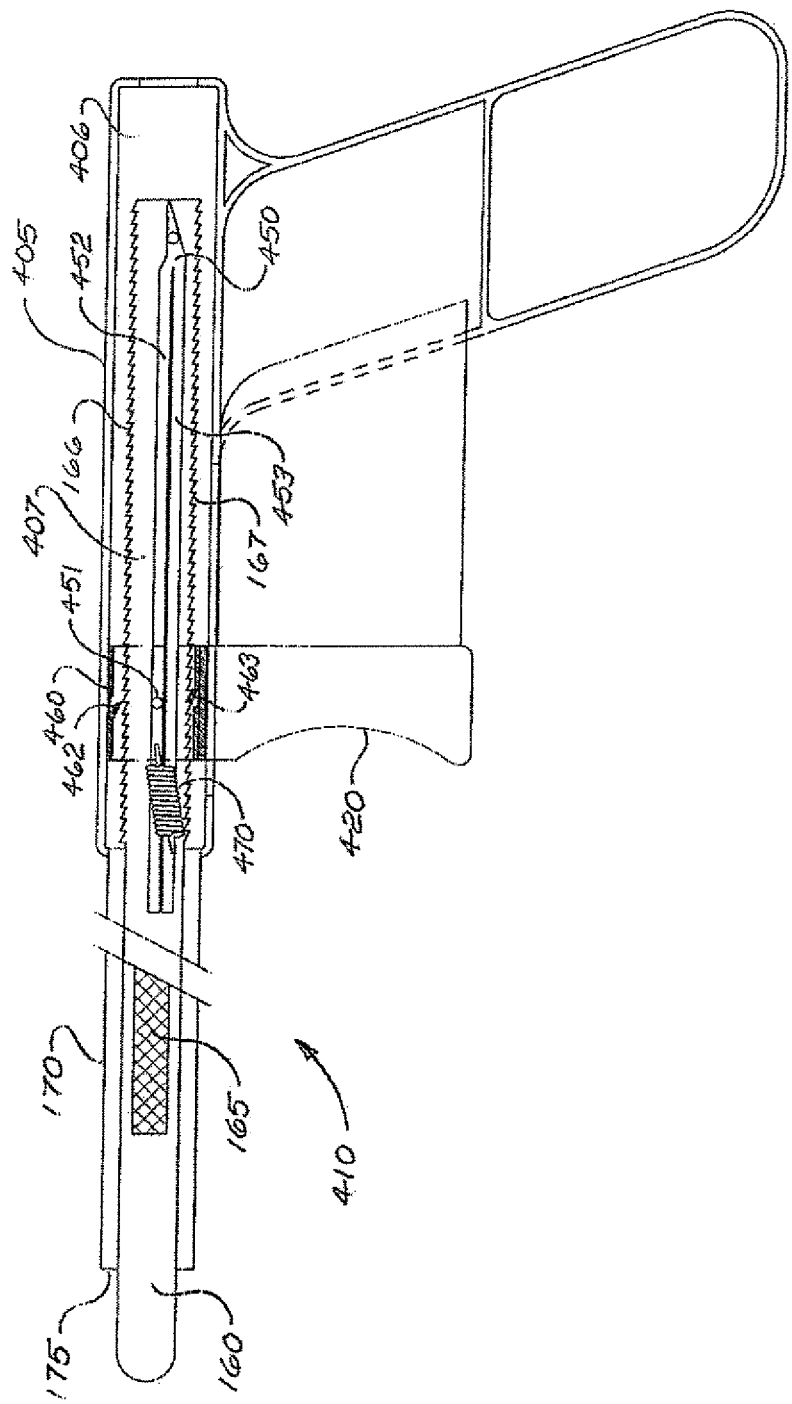
FIG. 20 is a side section view of a handle and actuator mechanism in accordance with various aspects of the present invention in, for example, a first condition.
Figure 21:
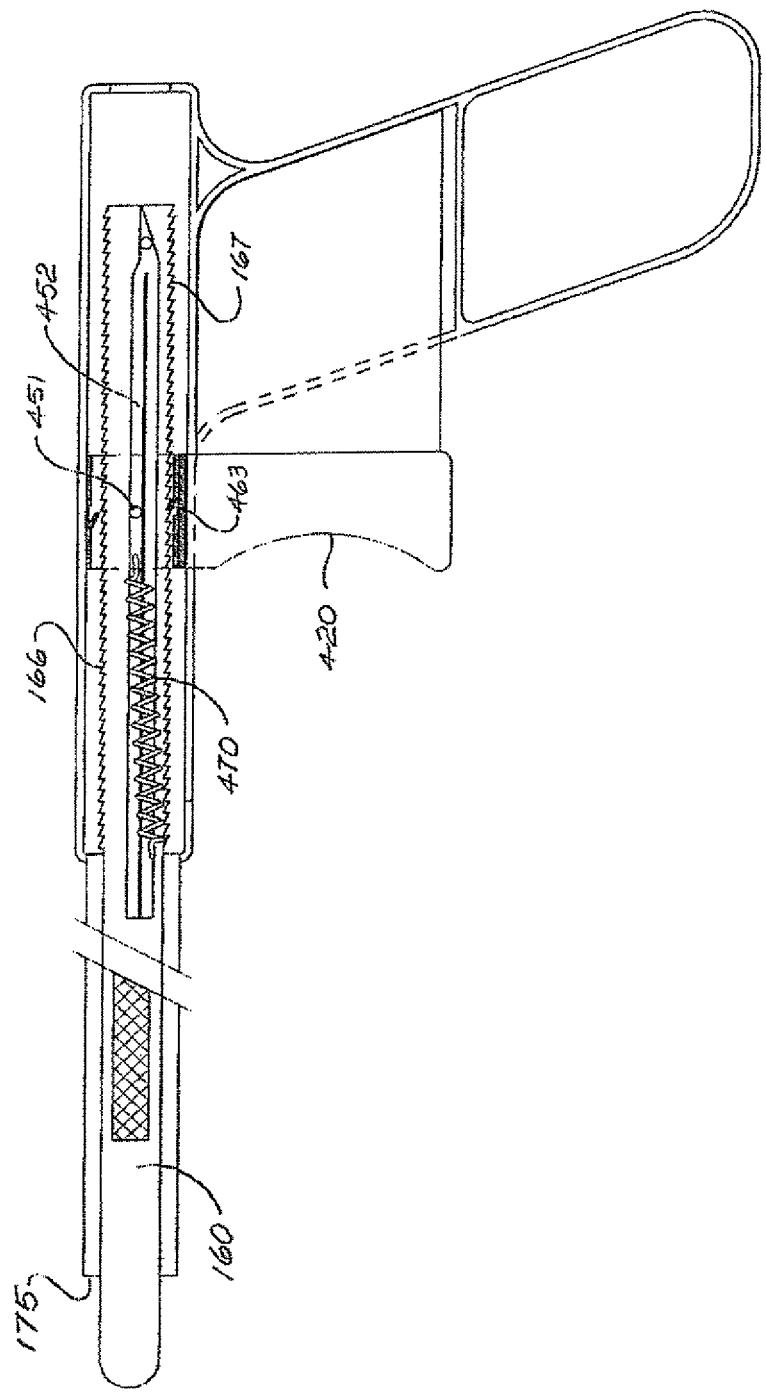
FIG. 21 is a side section view of a handle and actuator mechanism in accordance with various aspects of the present invention in, for example, a second condition.
Figure 22:
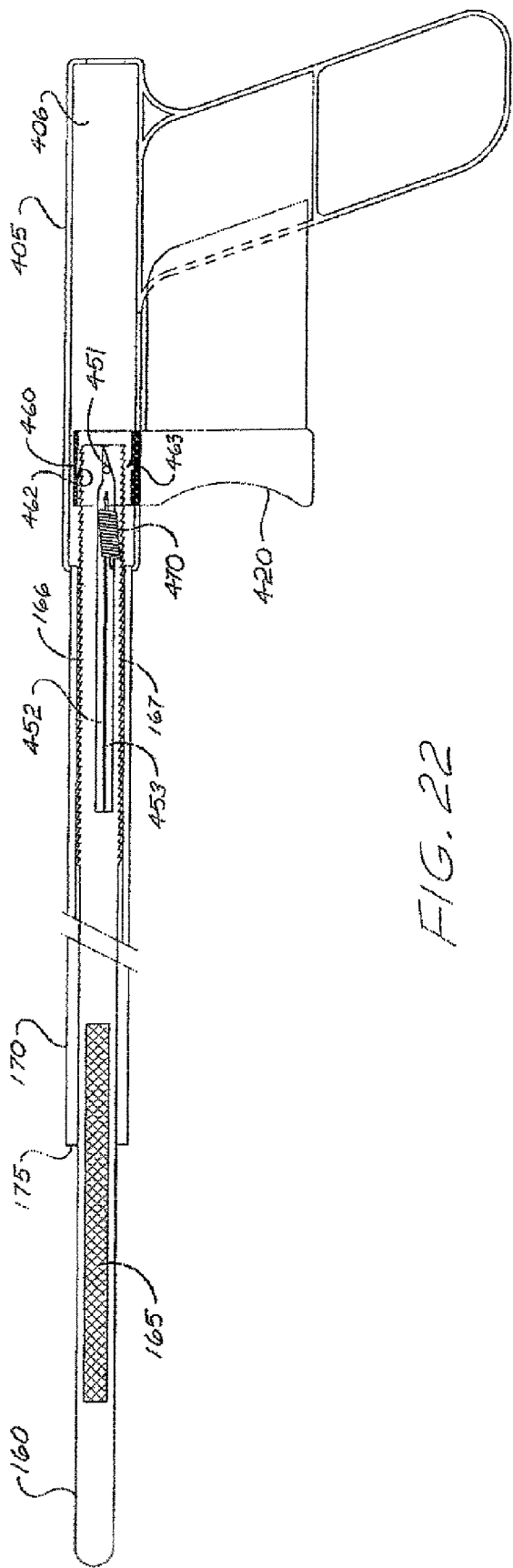
FIG. 22 is a side section view of a handle and actuator mechanism in accordance with various aspects of the present invention in, for example, a third condition.
Figure 23:
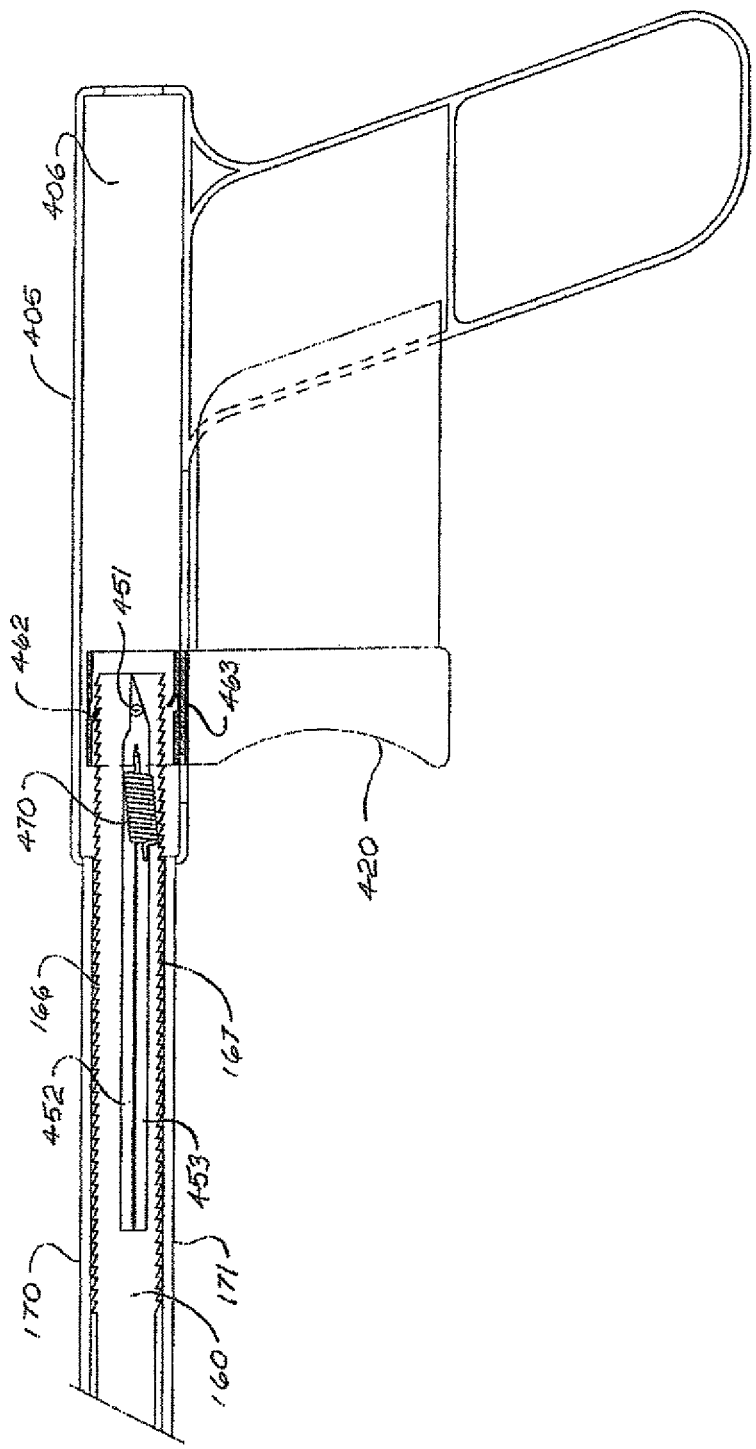
FIG. 23 is detailed side section view of a handle and actuator mechanism in accordance with various aspects of the present invention in, for example, a fourth condition.

In preparation for use or prior to deployment of the bag, as shown in FIG. 3, the containment pouch or bag 200 may be rolled or folded so that it will fit through an access port or trocar. The rolled bag 201 is attached to the distal end 175 of the elongate shaft 170 of the deployment device 100. In one aspect, the pouch or bag 200 is held in position by the drawstrings or tethers 250, 255 associated with the closing of the pouch or bag 200. When the containment pouch 200 is fully extended beyond the distal end of an access port or trocar, it is allowed to unroll and assume a generally flat configuration. The support arms 150, 160 are subsequently extended distally to fill the side pockets 270, 228 formed by the first hollow channel 225 of the pouch 200. The support arms 150, 160 assume a preformed shape upon extension from the distal end 175 of the elongate tubular shaft 170 of the deployment device 100. The support arms 150, 160 hold the pouch 200 in a condition that provides a large opening or open end 220 for introduction of materials 300 into the containment pouch 200.

Referring now to FIGS. 7-9, the deployment device 100, supports the introduction of the containment pouch 200 into a body cavity 30, deploys the pouch 200 and provides an appropriate opening 220 of the pouch 200. When the pouch 200 has been filled, the support arms 150, 160 are retracted. As the support arms 150, 160 retract, a tether or drawstring 250 associated with or attached to the central core support 149 begins to draw, unfold and invert a second or inverted portion 230 of the pouch 200 so that the inverted portion 230 of the pouch 200 covers the first opening portion 220 of the pouch 200. The inverted portion 230 covers the contaminated lip of the first opening 220 into which tissue 300 was placed. The second drawstring or tether 250 further closes the inverted portion 230. The first drawstring 255 simultaneously or sequentially moves as the second drawstring 250 moves to draw and close the first opening portion 220 of the pouch 200 allowing the pouch to be removed from a body cavity 30 without contaminating adjacent tissue or the incision site 42 through which it is withdrawn.

In one aspect, as the support arms 150, 160 retract, the tether or drawstring 255 associated with or attached to the central core support 149 begins to draw the first opening portion 220 of the pouch 200 closed. When the pouch 200 is substantially closed, the second tether or drawstring 250 unfolds and inverts a second or inverted portion 230 of the pouch 200 so that the inverted portion 230 of the pouch 200 covers the first opening portion 220 of the pouch 200. The inverted portion 230 covers the contaminated lip of the first opening 220 into which tissue 300 was placed. The second drawstring or tether 250 further closes the inverted portion 230 allowing the pouch to be removed from a body cavity 30 without contaminating adjacent tissue or the incision site 42 through which it is withdrawn.

Tissue is placed through the open end 220 of the containment pouch 200 and comes to rest in the closed end 215 of the bag 200. At the open end 220, a lip 227 is formed. Sides 210 of the bag connect the open end 220 to the closed end 215. As noted above, the bag in one aspect has an inverted portion 230. The inverted portion 230 extends from the open end 220 but folds down or towards the closed end 215 of the bag (FIG. 7). At the end of inverted portion 230, an open end or lip 237 is formed. The inverted portion 230 extends along the outside of the bag or generally along the sides 210 of the bag. As such, the bag can be divided into three sections or portions 200a,b, c. A first portion 200a holds or encompasses the open end 220 and/or the hollow channel 225. The second portion 200b extends from the open end 220 and is or represents the inverted portion 230 and thus encompasses or holds the second hollow channel 235. Likewise, the second portion 200b extends from the first portion along the outside of the bag and thus folds or covers over the first portion 200a. The third portion 200c extends from the first portion to the closed end 215. Thus, the third portion holds the tissue inserted into the bag. The third portion is larger than the first and/or the second portions. In one aspect, the sizes of the portions may vary to accommodate a smaller or larger bag, tissue or space in the body cavity and separation between the portions.

The first portion 200a of the bag is connected to the second 200b and third portions of the bag and positioned between the second and third portions of the bag. Thus, the first portion acts as a dividing line or portion between the second and third portions. In one aspect, the first portion comprises the drawstring 255 and the second portion 200b comprises drawstring 250 and thus allows the third portion 200c to be closed while allowing access to an intermediate enclosure of the second and first portions between the drawstrings 250 and 255. The intermediate enclosure in various aspects is arranged to hold additional tissue after the tissue first tissue is collected in the third portion 200c and/or inserted agents to test, absorb or shrink the tissue or portions of the tissue in the third portion. In one aspect, the drawstring 255 can be manipulated to reopen the bag or access to the third portion 200c, such that for example additional tissue or agents from the intermediate enclosure are combined with the tissue in the third portion 200c.

Referring to FIGS. 10-19 other aspects of a containment pouch or bag 200 are shown. The bag 200 comprises a plastic membrane formed into a watertight container having an open end 220, a closed end 215 and sides 210 connecting the closed end 215 to the open end 220. The first portion 200a and/or the open end 220 of the container is fitted with or formed with a seal retainer 321. In one aspect, the seal retainer 321 comprises two complementary retainer sections or halves 370, 371. The first retainer half 370 has one or more tongues, e.g., barbs or tongues 386, 387, extending from the half that mates with one or more corresponding cavities or grooves, e.g., grooves 388, 389, disposed in the second half 371 of the seal retainer 321. The retainer halves 370, 371 are portions of or separate or integrated channels of the bag 200 disposed along the entire or a portion of the outer periphery of the open end 220.

A sliding clasp 320 captures the two seal retainer halves 370, 371 biasing or pressing the two halves together. In one aspect, the clasp 320 and retainer halves 370, 371 are integrated as a single component. The clasp 320 is movable sliding along the length of the opening 220 of the pouch or bag 200 from a distal position or point to a proximal point. A drawstring or tether 400 in one aspect is attached to the clasp 320 such that the clasp 320 may be drawn from the distal position to the proximal position. In one aspect, the retainer 370, 371 is connected to or integrated with a first portion of the bag near or at the opening end 220 of the bag and is also connected to the drawstring 400. As such, the containment pouch 200 may be remotely closed while the bag is within a body cavity 30 by pulling upon the tether 400.

The retainer in one aspect comprises a pair of molded portions or halves 370, 371 arranged at the opening lip 227 of the pouch 200 that is sized and configured to receive the support arms 150, 160 within elongate support channels 380, 381 formed as part of the lip 227 of the pouch 200. As such, the tether 400 to be pulled upon to close the pouch 200 while the support arms 150, 160 are within the elongate support channels 380, 381. The tether 400 in one aspect is attached to the clasp 320 by threading it through, at least, a one or more apertures or loops, e.g., loops 382, 383, formed in the clasp 320. The clasp in one aspect is substantially rectangular and connected to first drawstring or tether 400 and in one aspect the clasp is made of a material that is different, e.g., harder or less resilient than, the drawstring or tether 400 and/or bag 200. The clasp 320 in one aspect is generally U-shaped with one or more folded portions 318, 319 such that the clasp 320 substantially surrounds the seal retainer halves 370, 371. The pouch 200 may be re-opened at any time by moving the clasp 320 distally. Thus, in one aspect, a movable clasp 320 is connected to the retainer 370, 371 and is movable from a first position (distal position) to a second position (proximal position) to close the bag and from the second position to the first position to open/re-open the bag.

Specifically referring now to FIGS. 17-19, the retainer 321 is associated with a first closable portion or opening lip 227 of the pouch 200 and a drawstring 250 is associated with a second closable portion or inverted lip 237 of the pouch 200. Also, as noted in FIGS. 7-9, the bag 200 may have three sections or portions 200a,b,c in which the first portion would hold the clasp 320. The clasp 320 is pulled upon to close the open end 220 along the lip 227 of the pouch 200 and, subsequently or in one aspect simultaneously, the drawstring 250 is pulled upon to invert the inverted portion 230 that has been folded over to the outside of the bag 200. As the inverted portion 230 inverts, the inverted portion 230 also draws closed along the lip 237 under the influence of the drawstring 250. In one aspect, the inverted portion is deflectable or biased to reorient itself from a folded position to an extended position, which facilitates the inversion initiated by the drawstring 250. As such, the inverted portion acts as or is a contamination or containment shield. The pouch or bag 200 in one aspect is released as the deployment device 100 is withdrawn. The support arms 150, 160 withdraw from the hollow channel 225 of the bag 200 as the arms are moved proximally within the deployment device 100.

With reference to FIGS. 20-23, in one aspect, a deployment device 410 is shown in operational phases. The deployment device 410 comprises an elongate tubular body 170, a handle 405 and an actuator, such as a trigger, slide or lever 420. The elongate tubular body 170 is sized and configured to operate through a laparoscopic access port or trocar. The proximal end of the elongate body 170 is attached to the handle 405. The handle 405 comprises a generally hollow portion having a cavity 406 sized and configured to hold a deployment regulator 407. In one aspect, the deployment regulator 407 has a reversible ratchet-clutch 460 that is coupled to and operable by the actuator 420. The ratchet clutch 460 is movable along a first and second defined pathway 452, 453.

In one aspect, the proximal portion of one or both support arms 150, 160 of the central core member has a plurality of projections or teeth 166, 167 that are acted upon or engaged in response to movement of the actuator 420. In one aspect, the actuator 420 is guided by, at least, a pathways 452, 453 acting as guide slots or ribs upon the support arms 150, 160 such that ratchet projections 462, 463 of the ratchet clutch 460 are selectively movable from a first, forward driving, condition to a second, rearward driving condition. The reversing of the driving conditions is timed by a reverse slot 450 of the pathways 452, 453 that forces the ratchet clutch 460 from a first position where the ratchet clutch 460 has a forward thrust to second position where the ratchet clutch 460 has a rearward thrust. A spring 470 attached between the ratchet clutch 460 and the actuator 420 provides a force that moves the ratchet clutch 460 distally along the first pathway 452 after it has been moved proximally by moving the actuator 420. The actuator 420 may be manipulated multiple times in one aspect to fully deploy and open the associated pouch or bag 200. When the pouch 200 is fully deployed and opened, the ratchet-clutch 460 moves to a second position along the second pathway 453 where the clutch 460 actively withdraws the central core support 149 and associated support arms 150, 160 from the pouch or bag 200. The tethers or drawstrings 250, 255 in one aspect are coupled to the central core support 149 and thus are tensioned or pulled upon as the central core 149 is moved proximally. In one aspect, the tethers or drawstrings 250, 255 are operated separately or sequentially.

The ratchet-clutch 460 in one aspect ensures that during closure of the bag 200 complete incremental closure of the bag and/or withdrawal of the support arms from the specimen bag are achieved. For example, by ensuring one way directional movement of the central core support 149 and/or support arms 150, 160, these components may not be partially withdrawn from the bag and then reinserted into the bag. If, for example, the support arms are withdrawn and reinserted but are not aligned with the channel of the bag, the support arms may be pushed through the bag or not support the bag. As such, an actuator 420 connected to the shaft 170 and having a ratchet-clutch 460 positions or movement of the at least one support arm can be regulated or controlled relative to the shaft. The ratchet-clutch 460 also prevents reinsertion of the support arms 150, 160 into the body cavity after the bag has been detached from the device. Reinsertion of the support arms could decrease visibility within the body cavity or the support arms could become entangled with the cord loop or with another device in the body cavity. The ratchet-clutch 460 counteracts this tensile force to prevent movement of the central core support and bag 200 in the distal direction relative to the shaft 170.

In FIGS. 24-26, the deployment devices provide various actuators 305-308 with various deployment regulators used to advance and support the support arms 150, 160. Moving an actuator, such as by rotating knob or thumb-wheel 305, sliding switch 306 or pivoting lever/trigger 307,308, causes or permits the central core support 149 and the support arms 150, 160 to move distally. For instance, the thumbwheel 305 associated with handle 315 rotates to advance or retract the central core support 149 and support arms 150,160. In one aspect, the slide 306 associated with handle 316 is moved to advance or retract central core support 149 and support arms 150, 160. Also, in one aspect, as shown, the handles 315-316 are in-line with the shaft 170 thereby reducing space occupied by the handles.

Engagement with corresponding teeth or projections 311-312 of respective actuators 305-306 maintains the position of the support arms 150, 160 relative to the handles 315-316. For instance, the thumbwheel 305 and the central core support 149 have corresponding mating notches and projections that are sized and configured to mate in a gear-like relationship or as a rack and pinion assembly. A user may rotate the thumbwheel in one direction to advance the support arms 150, 160 and subsequently rotate the thumbwheel in the opposite direction to retract the support arms. In one aspect, the slide 306 and the central core support 149 have corresponding mating notches and projections that are sized and configured to mate in a gear-like relationship or as a ratchet assembly. A user moves the slide in one direction to advance the support arms and subsequently move the slide in an opposite direction to retract the support arms. In one aspect, releasing or withdrawing the engagement or obstruction of the actuators 305 or 306 from the central core support 149 permits the movement of the core support 149 relative to the shaft 170.

In FIG. 26, a separate trigger or actuator 308 biased by spring 309 engages the central core support to frictionally maintain the position of the support arms 150, 160 relative to the handle. Releasing or withdrawing the engagement or obstruction of the actuator 308 from the central core support 149 permits the movement of the core support 149 relative to the shaft 170. The central core support 149 is urged in one direction by actuating the trigger 308 and pushing or allowing the core support to move forward or distally. In one aspect, a return spring 329 released by lever 307 allows the spring to extend biasing the core support in the proximal direction.

Releasing the trigger 308 holds the core support 149 in place axially. In one aspect, the central core support 149 and support arms 150, 160 retract as the lever 307 is actuated where it binds upon the central core support 149 causing the support to move rearward or proximally. The trigger 308 and a bind lock coupled to the lever 307 are sized and configured to be positioned between a generally perpendicular relationship with the central core support and an angular relationship with the central core support 149. The generally perpendicular position allows the central core support to slide freely through an opening within the respective trigger 308 or bind lock coupled to lever 307. When the trigger 308 or bind lock coupled to lever 307 is disposed or re-positioned to an angular orientation relative to the central core support, they bind upon the central core support in a traction-like relationship which holds the central core support and associate support arms 150, 160 in place until movement of the lever 307 and/or trigger 308.

Figure 27:
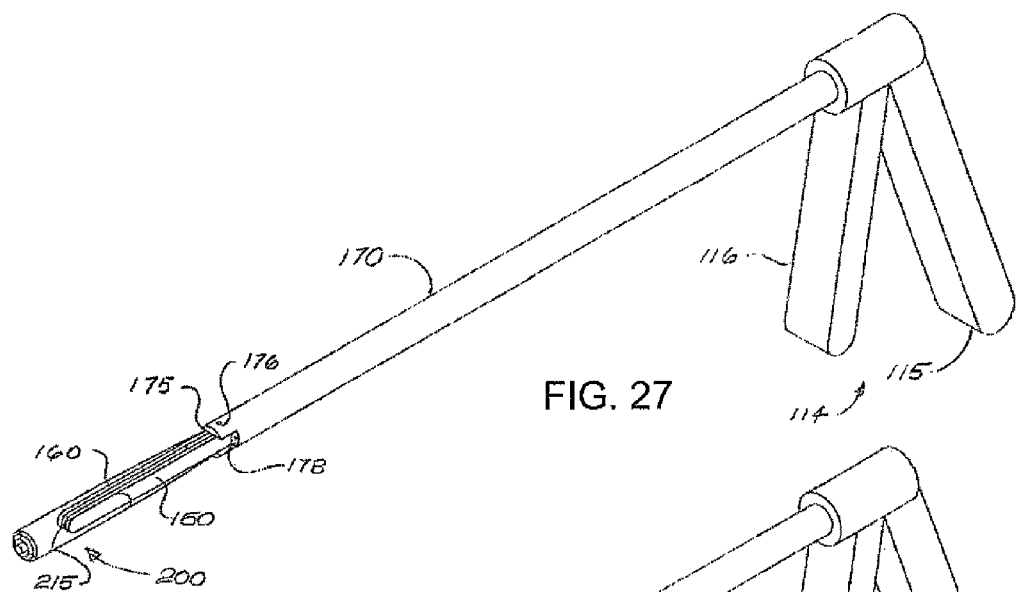
FIG. 27 is perspective view of a hinged jaw mechanism in accordance with various aspects of the present invention in for example a closed condition.
Figure 28:
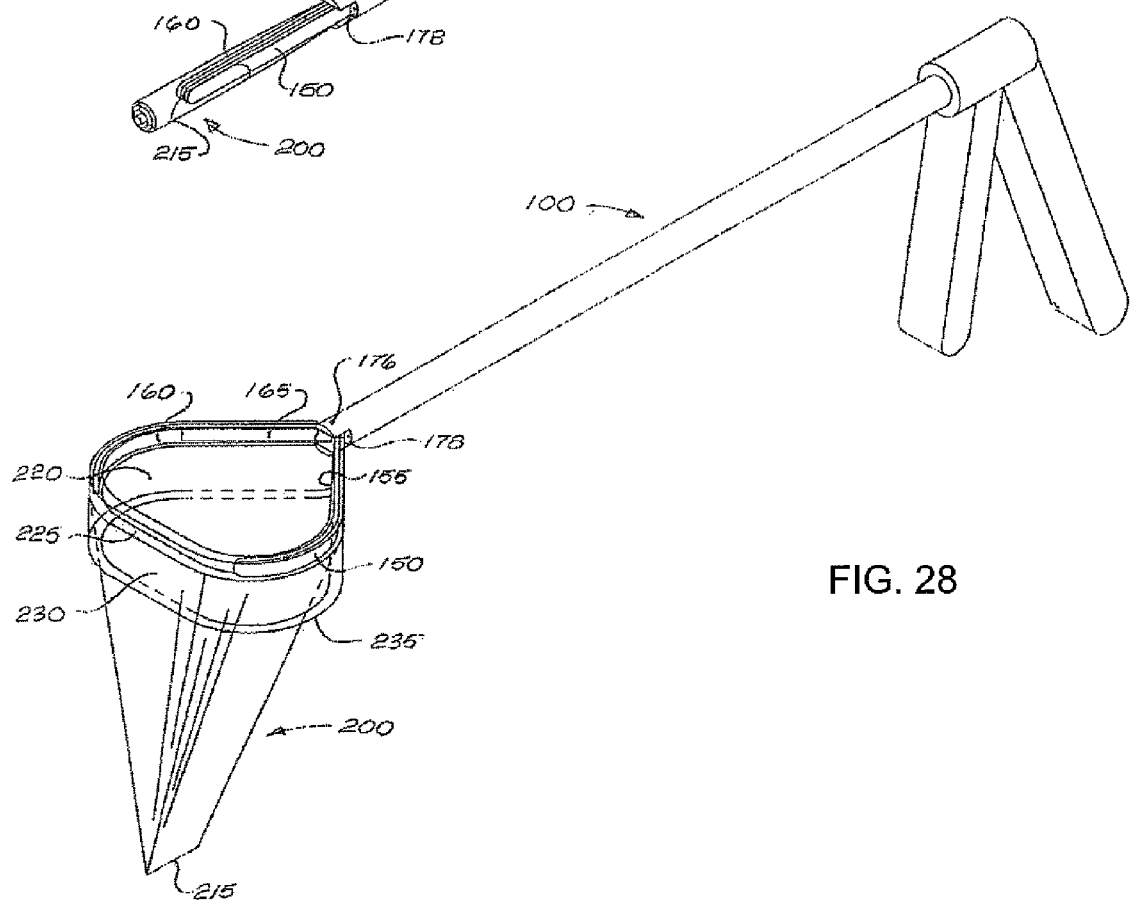
FIG. 28 is perspective view of a hinged jaw mechanism in accordance with various aspects of the present invention in for example an open condition.

In FIGS. 27-28, in one aspect, the deployment device 100 has one or more hinges 176 coupled to the support arms 150, 160 or extensions that are sized and configured to fit into the side channels formed by the first hollow channel 225 of the containment pouch. A movable handle or lever 116 associated with the actuator 114 urges the support arms 150, 160 from a first, closed condition to a second, open condition and subsequently returns the arms 150, 160 to a closed condition. The hinge or hinges 176 in conjunction with slots 178 in the shaft 170 allow the arms to pivot back and forth to the open and closed conditions. The arms 150,160 may be formed of a flexible material that provides support in specific regions. For instance, a rigid plastic material having a rectangular cross-section may allow the extended support arms 150, 160 to flex within the hollow channel 225 so that the opening 220 of the pouch 200 is generally rounded, but restrict deformation at a right angle to the opening plane of the containment pouch 200. In one aspect, the support arms 150, 160 are strengthened by reinforcement inserts 155, 165 placed at specific locations along each support arm 150, 160 that provides planar support. The support arms 150, 160 in one aspect comprise rigid metal members fitted with sleeves that provide a flexible distal portion for each support arm 150, 160 to aid in shaping the opening of the containment pouch 200 into a specific condition.

Figure 29:
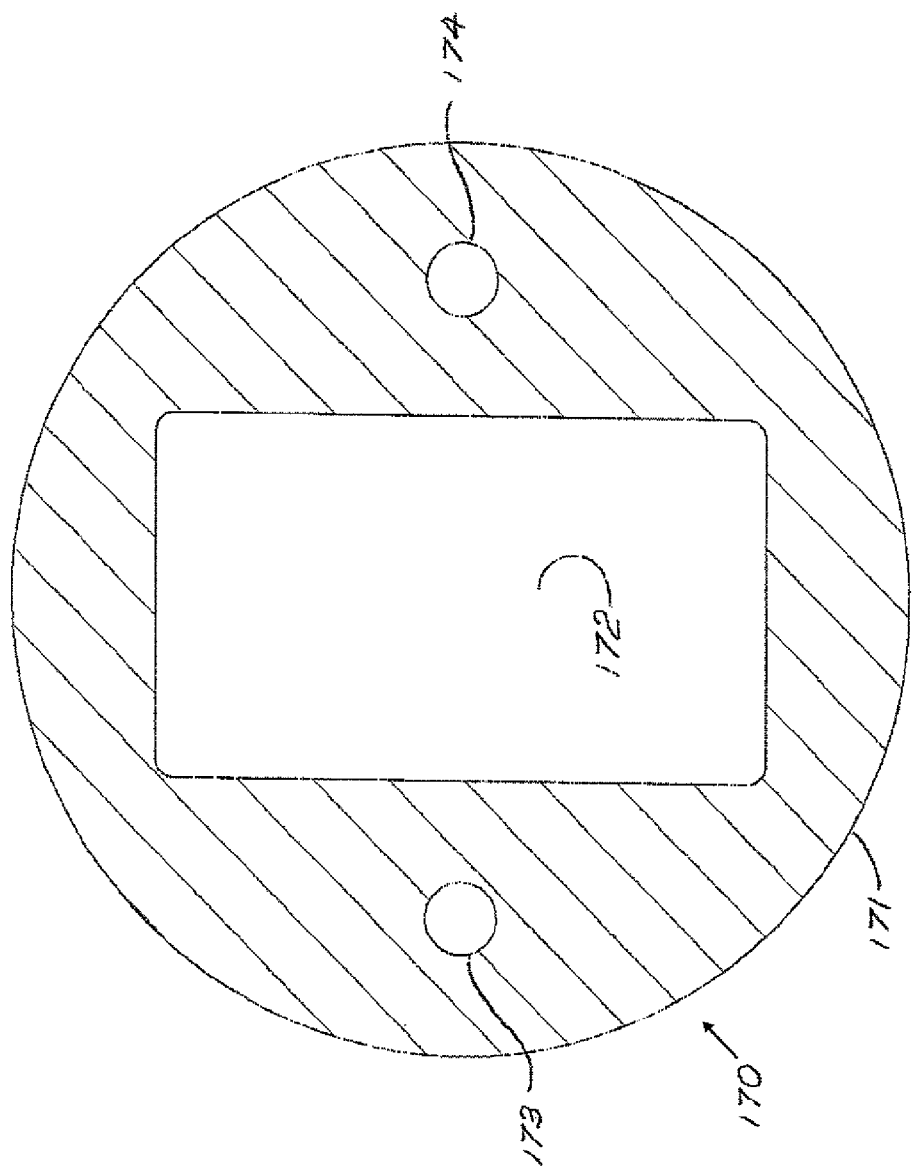
FIG. 29 is an end view of a deployment device in accordance with various aspects of the present invention.

In FIG. 29, the outer surface 171 of the tubular body or shaft 170 is generally smooth and symmetrical so that it may have a sealing relationship with the seals of a trocar in a working arrangement. In one aspect, there are three lumens 172, 173, 174 associated with the body 170. One of the lumens, the major lumen 172, in one aspect is rectangular in cross-section and is sized and configured to receive and hold, in alignment, the central core support 149 and support arms 150, 160 of the deployment device 100, 410. Two of the other lumens, minor lumens 173, 174, are positioned alongside the major lumen 172 on each side thereof to accommodate and/or guide the tethers or drawstrings 250, 255 associated with the containment pouch or bag 200. A construction of the elongate body 170 in one aspect comprises an extrusion of rigid plastic or metal, such as aluminum. The distal end 175 of the elongate body 170 is substantially open.

With reference to the various aspects described throughout, the containment pouch 200 comprises a plastic bag having a closed end 215, an open end 220 and an inverted portion 230. The containment pouch 200 is provided with a first hollow channel 225 formed circumferentially about the open end 220 and a second hollow channel 235 formed circumferentially about the open end of the inverted portion 230. The first hollow channel 225 forms a continuous pocket for the support arms 150, 160 of the deployment device 100 and a drawstring 255 for closing the containment pouch 200. The second hollow channel 235 forms a continuous channel for the drawstring 250 associated with inverted portion 230. The drawstrings 250, 255 may have slipknots 236, 226 in position adjacent to the openings of the hollow channels 235, 225 for drawing the openings of the pouch 200 closed. In various aspects, multiple clasps 320 and/or retainer 321 may be used in multiple portions of the bag or instead of slipknots. Likewise, the bag may have a single section or multiple sections having multiple drawstrings, slipknots and/or retainers. In one aspect, the containment pouch 200 is fitted onto the support arms 150, 160 and therefore comprises a disposable portion whereas the deployment device 100 may be reusable and sterilizable. Several containment pouches 200 in one aspect are packaged with one deployment device for use in a single surgical case.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A tissue isolation and removal device comprising:
   an elongate shaft defining a longitudinal axis having at least one support arm extending along the longitudinal axis from one end of the elongate shaft;
   a containment bag having an open end and a closed end opposite the open end, a first, second and third portion, the first portion of the containment bag supported by the at least one support arm to define the open end, the second portion extending from the first portion to a lip such that the at least one support arm is spaced from the lip, and the third portion extending opposite the second portion from the first portion to the closed end;
   a first drawstring coupled to the first portion, the first drawstring configured to close the third portion of the containment bag; and
   a second drawstring coupled to the second portion, the second drawstring spaced from the first drawstring such that the second portion is invertible about an axis generally parallel to the longitudinal axis between a first position in which it forms an inverted portion and a second position in which it forms a secondary cover shield over the third portion of the containment bag and wherein the second drawstring is movable to reposition the second portion from the first position to the second position.

2. The device of claim 1 wherein the third portion of the bag is larger than the first portion of the bag.

3. The device of claim 1 wherein the third portion of the bag is larger than the second portion of the bag.

4. The device of claim 1 wherein the first portion of the bag is connected to the second and third portions of the bag and positioned between the second and third portions of the bag.

5. The device of claim 1 wherein the first portion has a first hollow channel arranged to receive the at least one support arm and the second portion has a second hollow channel arranged to receive the second drawstring.

6. The device of claim 5 further comprising a reinforcement insert incorporated in the first hollow channel and arranged to receive the at least one support arm.

7. The device of claim 1 further comprising a retainer connected to the first portion of the bag and the first drawstring, the retainer including an elongate channel therein sized and configured to receive the at least one support arm.

8. The device of claim 7 further comprising a movable clasp connected to the retainer and movable from a first position to a second position, closing the bag and from a second position to a first position, opening the bag.

9. The device of claim 8 wherein the clasp is substantially rectangular and is connected to the first drawstring.

10. The device of claim 1 further comprising an actuator connected to the shaft and having a ratchet clutch regulating positions of the at least one support arm relative to the elongate shaft.

11. The device of claim 1 further comprising a reinforcement insert releasably connected to the at least one support arm.

12. The device of claim 1 further comprising a reinforcement insert having a proximal open end and a distal open end, the at least one support arm extending out of both the proximal open end and the distal open end and wherein the at least one support arm is hinged to the shaft.

13. The device of claim 1, wherein the second portion defines an intermediate enclosure when the third portion of the container bag is closed by the first drawstring.

14. The device of claim 1, wherein the at least one support arm comprises a corresponding at least one hinge such that the at least one support arm is pivotably actuatable about the hinge between a closed condition and an open condition.

15. The device of claim 1, wherein the first portion has a first hollow channel arranged to receive the at least one support arm and the first drawstring.

16. The device of claim 1, wherein the at least one support arm is selectively retractable from the first portion of the containment bag.

17. A tissue isolation and removal device comprising:
    a containment bag having an open end and a closed end opposite the open end, a first, second and third portion, the open end defined by the first portion, the second portion extending from the open end in a direction opposite the closed end to a lip, and the third portion extending from the first portion to the closed end;
    a first drawstring coupled to the first portion, the first drawstring extending circumferentially about the open end and defining a longitudinal axis of the containment bag, the first drawstring configured to close the open end of the bag to close the third portion of the containment bag; and
    a second drawstring coupled to the second portion, the second drawstring spaced from the first drawstring such that the second portion is invertible about the longitudinal axis to an unfolded position in which the second portion defines a secondary cover shield over the third portion of the containment bag and wherein the second drawstring is movable to invert the second portion to the unfolded position and to close the lip of the second portion.

18. The device of claim 17 wherein the first portion has a first hollow channel arranged to receive at least one support arm, the second portion has a second hollow channel arranged to receive the second drawstring and the third portion of the bag is larger than the second portion of the bag.

19. The device of claim 17 further comprising a movable clasp connected to the first portion of the bag and the first drawstring, the movable clasp is made of a first material and the first drawstring is made of a second material, the first material being different from the second material.

* * * * *